US00PP35060P3

(12) United States Plant Patent
Heyens

(10) Patent No.: US PP35,060 P3
(45) Date of Patent: Mar. 21, 2023

(54) ***CALATHEA* PLANT NAMED 'DRACAL01'**

(50) Latin Name: ***Calathea lietzei* E. Morren**
Varietal Denomination: DRACAL01

(71) Applicant: Dragontree Beheer B.V., Honselersdijk (NL)

(72) Inventor: Peter Heyens, Bangkok (TH)

(73) Assignee: Dragontree Beheer B.V., Honselersdijk (NL)

( * ) Notice: Subject to any disclaimer, the term of this patent is extended or adjusted under 35 U.S.C. 154(b) by 0 days.

(21) Appl. No.: 17/803,415

(22) Filed: Jun. 27, 2022

(65) Prior Publication Data

US 2022/0418178 P1 Dec. 29, 2022

(51) Int. Cl.
*A01H 6/12* (2018.01)
*A01H 6/00* (2018.01)

(52) U.S. Cl.
USPC ..... Plt./375

CPC ..... *A01H 6/12* (2018.05); *A01H 6/00* (2018.05)

(58) Field of Classification Search
USPC ..... Plt./375
See application file for complete search history.

(56) References Cited

PUBLICATIONS

CPVO hit on *Calathea* plant with no denomination, application No. QZ PBR 2021/1707, filed Jun. 25, 2021.*

* cited by examiner

*Primary Examiner* — Anne Marie Grunberg
(74) *Attorney, Agent, or Firm* — Samuel R. McCoy, Jr.

(57) ABSTRACT

'DRACAL01' is a new and distinctive variety of *Calathea* plant which is characterized by a fast rate of growth, large laminas borne on long petioles, a dark green upper foliar surface with unique multicolored variegation, a dark greyed-purple lower foliar surface with an irregular greyed-orange ring present, and the stability of all characteristics from generation to generation.

3 Drawing Sheets

Latin name of the genus and species: The Latin name of the genus and species of the novel variety disclosed herein is *Calathea lietzei* E. Morren.

Variety denomination: The inventive variety of *Calathea* disclosed herein has been given the variety denomination 'DRACAL01'.

CROSS REFERENCE TO RELATED APPLICATIONS

This application claims priority to the Community Plant Variety Rights application number 2021/1707, filed Jun. 25, 2021, which is herein incorporated by reference.

BACKGROUND OF THE INVENTION

Parentage: 'DRACAL01' originated as a naturally-occurring, partial plant mutation of an unnamed, variegated *Calathea lietzei* plant (not patented) discovered in January of 2021 at a commercial greenhouse in Bangkok, Thailand. The mutation was noted for its unique foliage variegation and was subsequently harvested from the parent plant, rooted in a nursery container, and grown to maturity to evaluate the distinctness and stability of the characteristics first observed. Upon confirmation of distinctness and stability, the new *Calathea* plant was selected for commercialization and given the name 'DRACAL01'.

Asexual Reproduction: Asexual reproduction of 'DRACAL01', by way of vegetative division of the plant, was first performed in the February of 2021 at a commercial greenhouse in Bangkok, Thailand and subsequently by meristematic tissue culture. Eight successive generations so produced have shown that the unique features of the instant cultivar are stable and reproduced true to type.

SUMMARY OF THE INVENTION

The cultivar 'DRACAL01' has not been observed under all possible environmental conditions and the phenotype may vary somewhat with variations in the instant environment such as temperature, day length, and light intensity, without, however, any variance in genotype. The following characteristics have been repeatedly observed and represent the distinguishing characteristics of the new *Calathea* cultivar 'DRACAL01'. These traits, in combination, distinguish 'DRACAL01' as a new and distinct cultivar.

1. *Calathea* 'DRACAL01' exhibits a fast rate of growth; and
2. *Calathea* 'DRACAL01' exhibits large laminas borne on long petioles; and
3. *Calathea* 'DRACAL01' exhibits a dark green adaxial foliar surface with a variegation pattern consisting of heavy blotching and suffusion with a combination of yellow-green and a mixture of greyed-yellow and greyed-green on the central portion of the lamina and portions of the lamina adjacent to and in between the secondary veins which is further bordered by an irregular, yet conspicuous, ring of yellow-green; and
4. *Calathea* 'DRACAL01' exhibits a dark greyed-purple abaxial foliar surface which transitions to dark green towards the margins and apex with an irregular, yet conspicuous, greyed-orange ring.

BOTANICAL DESCRIPTION OF THE PLANT

Figure 1:
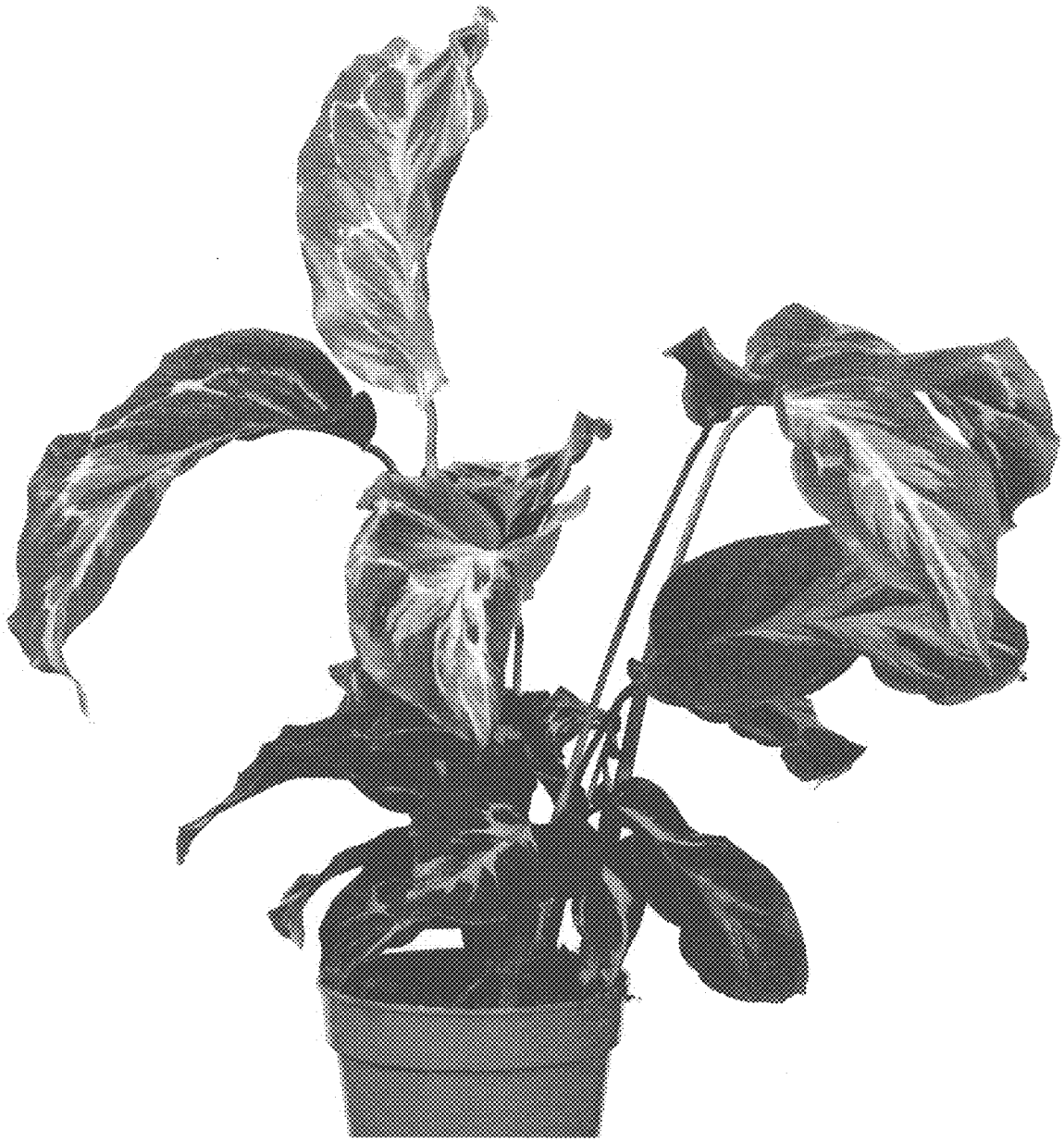
FIG. 1 shows, as nearly true as it is reasonably possible to make the same in color illustrations of this type, an exemplary 'DRACAL01' plant at approximately 12 month old, potted into a 12 cm nursery container, grown in a greenhouse in Honselersdijk, the Netherlands.
Figure 2:
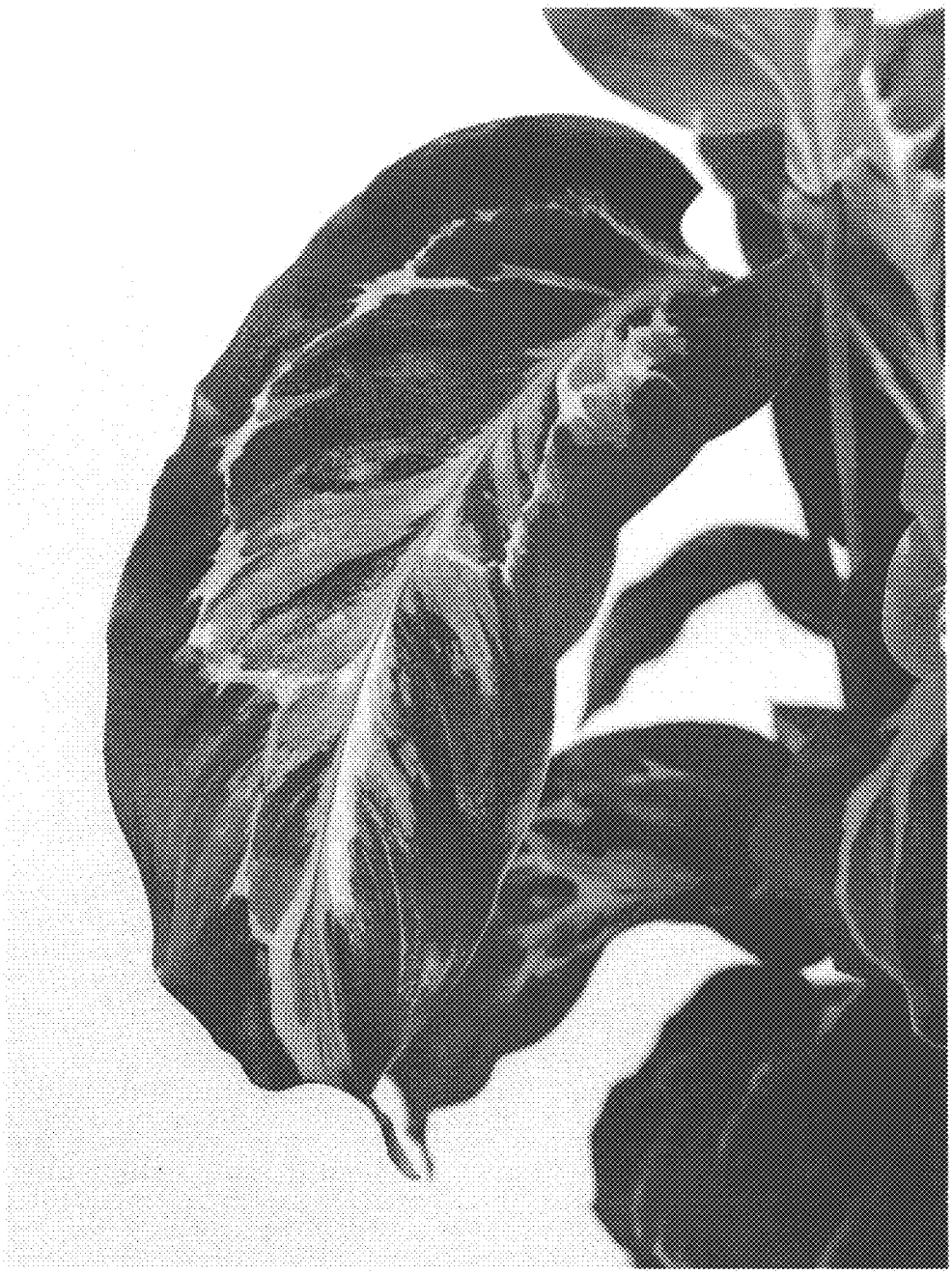
FIG. 2 shows, as nearly true as it is reasonably possible to make the same in color illustrations of this type, the typical adaxial surface of the mature foliage of 'DRACAL01'.
Figure 3:
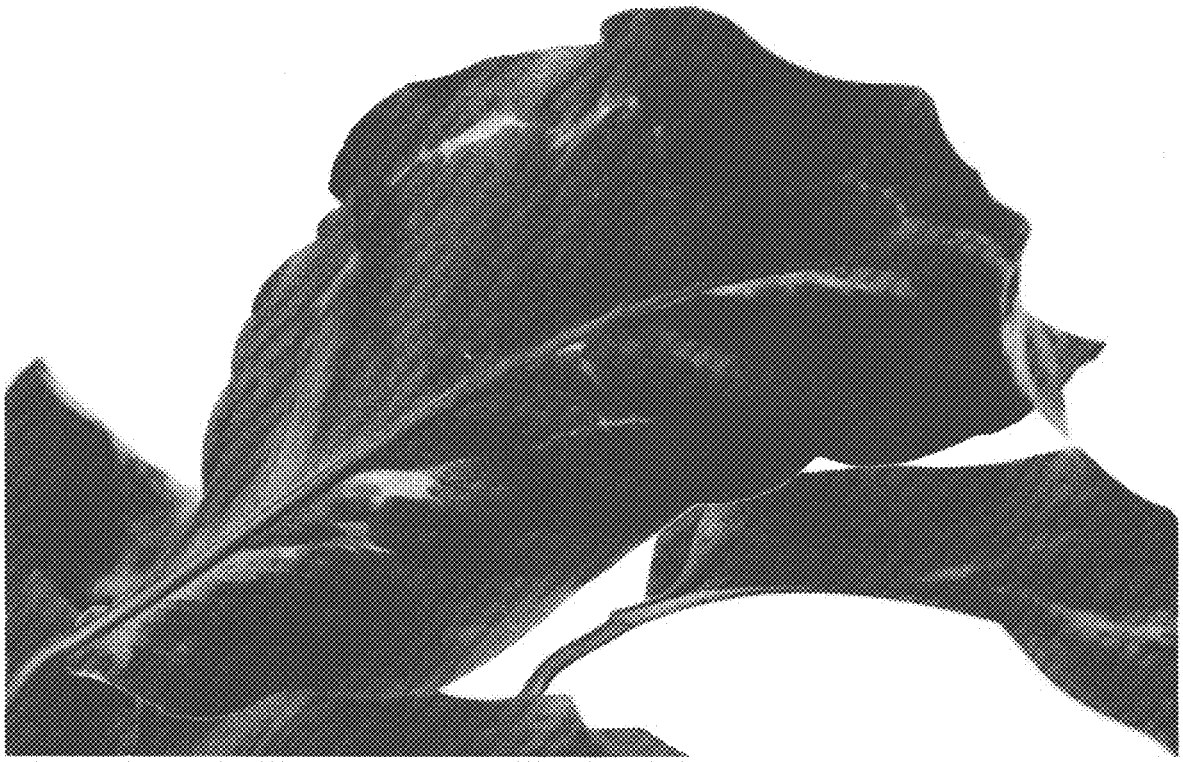
FIG. 3 shows, as nearly true as it is reasonably possible to make the same in color illustrations of this type, the typical abaxial surface of the mature foliage of 'DRACAL01'.

The following is a detailed botanical description of a new and distinct variety of *Calathea* known as 'DRACAL01', based upon observations of plants, approximately one year old from a rooted cutting, grown in 12 cm nursery container in a climate-controlled greenhouse in Honselersdijk, the Netherlands. Observation data was recorded in October of 2021. Plants were produced using conventional greenhouse production protocols for *Calathea* sp. which consisted of growing under shade with regular overhead irrigation and regular fertigation. No pest control measures were utilized and no photoperiodic treatments or artificial light was given to the plants.

Those skilled in the art will appreciate that certain characteristics will vary with older or, conversely, with younger plants. 'DRACAL01' has not been observed under all possible environmental conditions. Where dimensions, sizes, colors and other characteristics are given, it is to be understood that such measurements are approximations or averages set forth as accurately as practicable. The phenotype of the variety may differ from the descriptions set forth herein with variations in environmental, climactic and cultural conditions. Color notations are based on *The Royal Horticultural Society Colour Chart*, The Royal Horticultural Society, London, 2015 edition.

A botanical description of 'DRACAL01' and comparisons with the parent and the most similar variety of common knowledge are provided below.

General plant description:

*Growth habit*.—Clump-forming, upright, herbaceous perennial.

*Plant profile*.—Broad ovate.

*Growth rate*.—Fast growing.

*Plant vigor*.—Vigorous.

*Height*.—31.1 cm.

*Width*.—38.7 cm.

*Propagation*.—Mode of propagation — Vegetative division of plants and also meristematic tissue culture micropropagation. Time to initiate roots — Approximately 21 days to initiate roots at approximately 24 degrees Centigrade. Time to produce a finished plant — Approximately 10 weeks to produce a fully rooted cutting and 28 weeks to produce a marketable plant in a 12 cm nursery container.

*Environmental tolerances*.—USDA Zones 10 to 13; at least tolerant of temperatures of up to 40 degrees Celsius. Moderate to high tolerance to rain inundation; low tolerance to wind. Not drought tolerant.

*Pest resistance and susceptibility*.—Plants have not been observed to be susceptible or resistant to pathogens and pests common to *Calathea*.

Root system:

*Branching*.—Sparsely branched.

*Density*.—Moderately dense.

*Distribution*.—Roots are moderately deep.

*Diameter*.—0.2 cm.

*Texture*.—Fleshy; smooth; lacking root hairs.

*Color*.—Greyed-yellow, nearest to a mixture of RHS 161C and 161D.

Stems:

*Branching characteristics*.—Foliage emerges directly from the base of the plant; no lateral branching.

Foliage:

*Arrangement*.—Alternate; equitant.

*Division*.—Simple.

*Attachment*.—Petiolate.

*Quantity of leaves per shoot*.—Average of 3.

*Quantity of shoots per plant*.—Average of 6.

*Quantity of leaves per plant*.—Approximately 18.

*Lamina*.—Shape — Oblong to narrow ovate. Apex — Apiculate. Base — Acute. Aspect — Slightly to moderately carinate. Attitude — Upright and outward. Dimensions — 19.6 cm long and 8.5 cm wide. Margin — Entire; moderate undulation. Texture and luster, adaxial surface — Smooth, glabrous, and slightly glossy. Texture and luster, abaxial surface — Smooth, glabrous, and matte. Juvenile color, adaxial surface — Green, nearest to RHS NN137A. The central portion of the lamina and portions of the lamina adjacent to and in between the secondary veins are heavily blotched and suffused with a combination of green, yellow-green, and a mixture of greyed-yellow and greyed-green; RHS 138A, 146D, 147C, and a mixture of 160C and 195B. Juvenile color, abaxial surface — Greyed-purple, nearest to RHS N187A, and transitioning to green towards the apex and margins, nearest to RHS 138B. Portions of the lamina that are adjacent to and in between the secondary veins are heavily blotched and suffused with a combination of yellow-green and greyed-red; nearest to RHS 150D, 182B and 182C. Mature color, adaxial surface — Green, nearest to a mixture of RHS 136A and 139A, with an irregular yellow-green ring on the lamina, nearest to RHS N144A, N144B, 150A and 150B. The central portion of the lamina and portions of the lamina adjacent to and in between the secondary veins are heavily blotched and suffused with a combination of yellow-green and a mixture of greyed-yellow and greyed-green; RHS NN137B, 138A, 147B, and a mixture of 154C and 160C. Mature color, abaxial surface — Greyed-purple, nearest to RHS N187A, and transitioning to green towards the apex and margins, nearest to RHS NN137A, with an irregular greyed-orange ring on the lamina, nearest to RHS 177C and 177D. Portions of the lamina that are adjacent to the main vein are suffused with yellow-green, nearest to RHS 149C and 149D. Venation — Vein pattern — Pinnate. Vein color, adaxial surface — Green, nearest to RHS 138B. Vein color, abaxial surface — Greyed-orange, nearest to RHS 177B.

*Petiole, excluding geniculum*.—Length — Approximately 20.5 cm. Width — Approximately 0.5 cm at the proximal end and 0.325 cm at the distal end. Strength — Strong. Texture — Smooth and glabrous. Luster — Moderately glossy. Color, adaxial surface — Yellow-green, nearest to RHS 148A, and fading to a lighter shade of yellow-green towards the proximal end, nearest to RHS N148B. Color, abaxial surface — Yellow-green, nearest to RHS 148A, and fading to a mixture of yellow-green and greyed-green towards the proximal end, nearest to RHS N148B and 195B. Geniculum — Length — Approximately 1.9 cm. Width — Approximately 0.375 cm. Color — Nearest to a mixture of greyed-orange and brown, RHS 177A and 200C. Sheath — Length — 11.4 cm. Width — Approximately 0.6 cm. Color, adaxial surface — Yellow-green, nearest to RHS N148B, and very lightly suffused with purple towards the margins, nearest to RHS N77D. Color, abaxial surface — Yellow-green, nearest to RHS 148B, and very lightly suffused with purple towards the margins, nearest to RHS N77D.

Inflorescence: No flowers observed to date.
Flower bud: No flowers observed to date.
Flower: No flowers observed to date.
Reproductive organs: No flowers observed to date.
Seed and fruit: No flowers observed to date.

COMPARISONS WITH THE PARENTS

Plants of the new cultivar 'DRACAL01 ' differ from its parent, an unnamed variegated *Calathea* plant (not patented), by the characteristics described in Table 1.

TABLE 1

| Characteristic | 'DRACAL01' | The parent. |
|---|---|---|
| Rate of growth. | Faster than the parent. | Slower than 'DRACAL01' |
| General coloration of the mature foliage; adaxial surface. | Dark green with a variegation pattern consisting of heavy blotching and suffusion with a combination of yellow-green and a mixture of greyed-yellow and greyed-green on the central portion of the lamina and portions of the lamina adjacent to and in between the secondary veins which is further bordered by an irregular, yet conspicuous, ring of yellow-green | Variegated and marbled with green and a light greyed-green coloration. |

TABLE 1-continued

| Characteristic | 'DRACAL01' | The parent. |
|---|---|---|
| | | |

COMPARISONS WITH THE MOST SIMILAR VARIETY OF COMMON KNOWLEDGE

Plants of the new cultivar 'DRACAL01' may be distinguished from the commercial variety *Calathea* 'Fusion White' (U.S. Plant Pat. No. PP26,187) by the combination of characteristics described in Table 2.

TABLE 2

| Characteristic | 'DRACAL01' | 'Fusion White' |
|---|---|---|
| Foliage size. | Larger than 'Fusion White'. | Smaller than 'DRACALO01'. |
| General coloration of the mature foliage; adaxial surface. | Dark green with a variegation pattern consisting of heavy blotching and suffusion with a combination of yellow-green and a mixture of greyed-yellow and greyed-green on the central portion of the lamina and portions of the lamina adjacent to and in between the secondary veins which is further bordered by an irregular, yet conspicuous, ring of yellow-green | Variegated and marbled with green and white. |
| General coloration of the mature foliage; adaxial surface. | Lighter shade of greyed-purple, relative to 'Fusion White, transitioning to dark green towards the margins and apex, and an irregular, yet conspicuous, greyed-orange ring. | Darker shade of greyed-purple, relative to 'DRACAL01'. |

That which is claimed is:

1. A new and distinct variety of *Calathea* plant named 'DRACAL01', substantially as described and illustrated herein.

* * * * *